United States Patent
Loffredo

(10) Patent No.: US 10,507,113 B2
(45) Date of Patent: Dec. 17, 2019

(54) REVERSE TOTAL HIP REPLACEMENT

(71) Applicant: Nicholas John Loffredo, North Chili, NY (US)

(72) Inventor: Nicholas John Loffredo, North Chili, NY (US)

( * ) Notice: Subject to any disclaimer, the term of this patent is extended or adjusted under 35 U.S.C. 154(b) by 0 days.

(21) Appl. No.: 16/273,339

(22) Filed: Feb. 12, 2019

(65) Prior Publication Data

US 2019/0167436 A1    Jun. 6, 2019

Related U.S. Application Data

(62) Division of application No. 15/225,873, filed on Aug. 2, 2016, now Pat. No. 10,245,149.

(Continued)

(51) Int. Cl.
| | | |
|---|---|---|
| A61F 2/34 | (2006.01) | |
| A61F 2/36 | (2006.01) | |
| A61F 2/46 | (2006.01) | |
| A61B 17/16 | (2006.01) | |
| A61B 17/17 | (2006.01) | |

(Continued)

(52) U.S. Cl.
CPC ............ *A61F 2/34* (2013.01); *A61B 17/1666* (2013.01); *A61B 17/1746* (2013.01); *A61F 2/3603* (2013.01); *A61F 2/3609* (2013.01); *A61F 2/4609* (2013.01); *A61B 17/86* (2013.01); *A61F 2002/305* (2013.01); *A61F 2002/30332* (2013.01); *A61F 2002/30878* (2013.01); *A61F 2002/3483* (2013.01); *A61F 2002/3615* (2013.01); *A61F 2002/4629* (2013.01); *A61F 2002/4687* (2013.01)

(58) Field of Classification Search
CPC ........ A61F 2/34; A61F 2/3603; A61F 2/3609; A61F 2/3601

See application file for complete search history.

(56) References Cited

U.S. PATENT DOCUMENTS

| | | |
|---|---|---|
| 3,916,451 A | 11/1975 | Buechel |
| 8,747,481 B2 | 6/2014 | Maurer |

(Continued)

FOREIGN PATENT DOCUMENTS

| | | |
|---|---|---|
| EP | 3 053 547 | 8/2016 |
| FR | 2882921 | 9/2006 |

OTHER PUBLICATIONS

Canale, T., Beaty, J. (2008). Campbells Operative Orthopedics. Philadelphia,PA: Mosby Elsevier. vol. 1, pp. 312-482.

(Continued)

*Primary Examiner* — Kristen Matter
(74) *Attorney, Agent, or Firm* — Louis S. Horvath; John A. Agostinelli

(57) ABSTRACT

A reverse total hip prosthesis is characterized by a femoral cup component and an acetabular ball component and is used for reconstruction of a hip joint. The prosthesis reverses the mechanics across the joint medializing the center of rotation, preventing dislocation in a posterior direction. Both ball and socket portions of the components lie outside of bone enabling larger sizing of the femoral and acetabular components improving stability, regardless of the size of the patient's anatomy. A method for reverse hip prosthesis implantation eliminates reaming through the base of the acetabulum preserving acetabular bone stock.

10 Claims, 10 Drawing Sheets

Related U.S. Application Data

(60) Provisional application No. 62/282,472, filed on Aug. 3, 2015.

(51) Int. Cl.
*A61B 17/86* (2006.01)
*A61F 2/30* (2006.01)

(56) References Cited

U.S. PATENT DOCUMENTS

| | | | |
|---|---|---|---|
| 8,992,627 | B2 | 3/2015 | Termanini |
| 10,245,149 | B2 * | 4/2019 | Loffredo .................... A61F 2/34 |
| 2006/0058887 | A1 | 3/2006 | DeSmet et al. |
| 2007/0156246 | A1 | 7/2007 | Meswania |
| 2007/0173945 | A1 | 7/2007 | Wiley |
| 2010/0191246 | A1 | 7/2010 | Howald et al. |
| 2011/0218637 | A1 | 9/2011 | Termanini |
| 2013/0345823 | A1 | 12/2013 | Termanini |
| 2014/0025178 | A1 | 1/2014 | Termanini |
| 2014/0156011 | A1 | 6/2014 | Termanini |
| 2014/0200675 | A1 | 7/2014 | Termanini |
| 2016/0058559 | A1 | 3/2016 | Forsell |

OTHER PUBLICATIONS

Brand, R., Mont, M., Manring, M. (2011). Biographical Sketch: Themistocles Gluck (1853-1942). Journal of Orthopedic Related Research, 469(6): 1525-1527.

Brown, D., Neumann, R. (2004) Orthopedic Secrets. 3RD Ed. Philadelphia,PA: Hanley&Belfus. pp. 261-263.

Drake, G., O'Connor, D., Edwards, T. (2010). Indications for Reverse Total Shoulder Arthroplasty in Rotator Cuff Disease. Journal of Clinical Orthopedics, 468(6).

Yang, C., Goodman, SB. (2009). Outcome and Complications of Constrained Acetabular Components. Journal of Orthopedics, 32(2).

Powell, J., Belzile, E., Antoniou, J., Vendittoli P., Smith, F., Naudie, D., et al. (2014). The Bone & Joint Journal.

* cited by examiner

REVERSE TOTAL HIP REPLACEMENT

CROSS-REFERENCE TO RELATED APPLICATION

The present application is a Divisional of an earlier-filed application, U.S. Ser. No. 15/225,873 entitled "Reverse Total Hip Replacement" in the name of Nicholas John Loffredo and filed Aug. 2, 2016, which claims priority to U.S. Provisional Application No. 62/282,472 filed Aug. 3, 2015, also in the name of Nicholas J. Loffredo.

FIELD OF THE INVENTION

The invention relates generally to a hip replacement arthroplasty with the reversal of the traditional components. More specifically, the invention relates to a reverse total hip replacement with a femoral component that has a cup shaped articulating surface and an acetabular component that is characterized as a spherical segment having a spherical articulating surface portion.

BACKGROUND OF THE INVENTION

In regards to total hip arthroplasties Themistocles Gluck attempted the first hip femoral head arthroplasty with ivory implants in 1891 (Brand, Mont, & Manring, 2011). Since that time the total hip replacement has undergone a continually evolving spectrum of advancements in medical science. The evolution of the total hip replacement has led components to become stronger, more versatile, and wear resistant. Today's total hip replacements are said to potentially last indefinitely by their manufacturers. The total hip replacement has been at the center of medical technical advancements from perfecting the technique of hip surgical approaches to recent innovations in medications that reduce operative blood loss.

In 2006 the FDA approved the Birmingham Hip Resurfacing system (Canale, 2008). This new prosthesis allowed for a hip replacement without resection of the femoral neck. The femoral component allows for less bone resection than a total hip replacement. Many orthopedic surgeons began using this new innovative prosthesis until clinical studies showed an increase risk of femoral neck fracture in women (Powell, Belzile, Antoniou, et al., 2014). This is an important lesson that not all medical advancements are truly the next gold standard but each can provide an important step forward nonetheless, even if by trial and error.

The current standard total hip replacement is made from a chromium-cobalt alloy with two main components. The femoral component consists of a femoral intramedullary stem and neck with interchange head attachments. The femoral component has a spherical articulating head. The acetabular component is typically a metal alloy cup with a plastic polymer inner cup insert. The femoral component recreates the ball of the joint while the acetabular component recreates the cup.

The surgical procedure involved to insert the total hip replacement involves creating an osteotomy at the base of the femoral neck and reaming the intramedullary canal to implant the femoral component. The acetabular component is prepared by using sequential hemi-spherical reamers to prepare an acetabular bed that mimics the dimensions of the acetabular component.

A major source of focus of design modifications with the current total hip replacement is to minimize the rate of dislocation. Currently the dislocation rate in the US in regards to total hip replacements is 1-2% (Brown & Neumann, 2004). This is not a large number but for those patients unfortunate enough to experience a dislocation the repercussions can be devastating. Currently modifications to the total hip replacements include the use of large femoral heads, proper cup alignment, and thinner cup liner to accommodate the larger femoral heads. A potential solution for solving the problem of total hip prosthesis dislocation is to reverse the design of the components.

The concept of a reverse joint prosthesis has been previously described in patent US20070173945 by applicant Zimmer Technology, Inc. This design utilizes a reverse joint prosthesis of the shoulder. The shoulder joint prosthetic system shows a glenosphere component implanted into the humerus. This component then articulates with a humeral cup component which is implanted into the glenoid. This design is referred to currently as a reverse total shoulder prosthesis. The reverse total shoulder prosthesis is currently indicated for use to restore shoulder motion in patients with advanced rotation cuff disease (Drake, G., O'Connor, D., Edwards, T. (2010). Indications for Reverse Total Shoulder Arthroplasty in Rotator Cuff Disease. Journal of Clinical Orthopedics, 468(6)). This teaching of the shoulder joint prosthetic system makes no mention of the use of this prosthesis in the hip joint.

Implanting this device into the hip joint would most certainly fail for a multitude of reasons. The glenoid component is a stemmed component that utilizes a press-fit technique to gain bony purchase. This glenoid component could not be implanted into the acetabulum because of the limited bone stock in the medial wall of the acetabulum. The proximal humerus does not have a narrowing or neck below the articular surface. Therefore, this design would not be suitable for the hip because the femoral head has an anatomic neck which aligns the articular surface at 125 degrees from the shaft. This allows for stability through the joint with weight bearing.

The concept of a reverse total hip prosthesis has been described in publication US20110218637 by applicant Zafer Termanini in 2010. The patent design utilized an interlocking reverse hip prosthesis. A similar interlocking reverse total hip prosthesis was described in US20140025178 by applicant Hip Innovation Technology Llc in 2013. The interlocking design means that the acetabular and femoral components are joined together. The concept is beneficial because in theory this would eliminate the chance of dislocation. In reality the use of interlocking or constrained total hip prosthesis has widely fallen out of favor. The failure rate in long term follow up associated with constrained total hip prosthesis has been shown to be as high as 42 percent (Yang, Goodman, 2009). This failure is a result of loosening of the acetabular component which is ultimately pulled away from the pelvis secondary to the interlocking design (Yang, C., Goodman, S B. (2009). Outcome and Complications of Constrained Acetabular Components. Journal of Orthopedics, 32(2).).

A reverse total hip prosthesis was also described in U.S. Pat. No. 8,747,481 by applicant Brian Ted Maurer in 2012. This design did not include an interlocking system, though, this design has many practical limitations for clinical use. In the patent drawings, FIG. 12, elements 120 and 102 articulate with each other. In reality the design of the interaction between these two surfaces will entrap soft tissue and scar formation. Furthermore, this design is especially prone to acetabular loosening because element 118 of the FIG. 12 creates a lever arm with weight bearing on the acetabular component base. This post will create a rotational force on the acetabular base shearing it from the pelvis.

SUMMARY

The present disclosure relates to hip prostheses and methods of use for patients with damaged hip joints that require a total hip replacement. The disclosure relates to a reverse total hip replacement and comprises a femoral and acetabular component. This reverse prosthesis changes the femoral component from the ball surface of the joint to the cup, and the acetabular component changes from the cup portion of the joint to the ball.

This method effectively reverses the native articulating biomechanics of the ball and socket hip joint. The reverse total hip prosthesis medializes the center of rotation of the hip joint. Therefore, this method provides an advantage to the standard total hip replacement because the reverse prosthesis requires less force for the abductor muscles to move the joint. This can be an important advantage with revision surgery when surrounding soft tissue is scarred or damaged from previous surgery or infection.

The reverse total hip replacement is advantageous because the native dimensions of the human do not dictate the size of the femoral component cup or acetabular ball. In the reverse total hip replacement, these aspects of the prosthesis lie outside of the bony walls of the acetabulum, enabling the largest sized head and cup to be used in a small individual.

The reverse total hip replacement is further advantageous in this regard because while the standard total hip replacement is most susceptible to dislocation posterior in high flexion of the hip, the reverse total hip replacement is not. The method of the present disclosure has the added benefit of effectively reversing the biomechanics of the joint. Therefore, the reverse total hip would be most susceptible to anterior dislocation which is far less common than posterior dislocation. The human hip can only achieve approximately 20 degrees of extension while the hip flexes to over 120 degrees making posterior dislocation a more likely culprit in standard total hip replacements.

The disclosed method also has an advantage to the standard hip replacement because it does not require reaming of the medial wall of the acetabulum. This is most beneficial because this wall of the acetabulum can be thin and lead to migration of the cup into the pelvis. The medial wall of the acetabulum can be exceptionally thin or nonexistent in revision total hip replacements where previous bone reaming has already occurred. The reverse design places the ball component on the acetabular side. Therefore, the acetabular reamer need not be hemispherically shaped. The apex of the spherical portion of the reamer need not exist. Thus, the reamer can substantially take on the shape of a spherical segment, defined as a portion of a sphere that has been cut by parallel planes. This enables more bone to be spared from resection during the procedure.

The reverse total hip replacement can also enable fastener fixation of the acetabular component in a transverse fashion. Current practice is to place lag screws into the cup that aim the screw trajectory into the true pelvis and collinear to vital organs. The reverse total hip replacement enables screw fixation along a trajectory that traverses the cup perpendicular to the current practice path of acetabular cup screws. The inventive design does not aim fasteners directly at important neurovascular structures and organs of the pelvis.

Thus in one aspect the disclosure relates to a reverse hip replacement prosthesis device comprising a femoral component and an acetabular component for implantation into a human femur and a human acetabulum wherein the femoral component further comprises a cup portion and a stem portion for implantation to the human femur and wherein the cup portion attachably accepts a saucer-shaped spacer. The acetabular component further comprises an acetabular ball which fixes to an acetabular base for implantation into the human acetabulum, the acetabular base having substantially the shape of a spherical segment at its interface with the acetabulum, thereby preserving the native thickness of the medial acetabulum. The femoral component replaces a portion of a human femur and the acetabular component replaces the acetabular human socket, and wherein the cup portion of the femoral component articulates with the acetabular ball, thereby reversing the human articulating biomechanics of ball and socket hip joints.

In another aspect, the disclosure relates to a targeting guide for alignment of acetabular base attachment fasteners, the targeting guide comprising an acetabular base arm for removably connection to a central barrel of the acetabular base. The targeting guide further comprises an attachment fastener arm for guiding the attachment fasteners into the acetabulum. The attachment fastener arm further comprises cannulated fastener sleeves for enabling the alignment of the attachment fasteners with respect to the orientation of the acetabular base and the desired trajectory of the attachment fasteners in the human acetabulum. An alternative option exists to drill the pilot holes for the screws through the post guide without first placing a guide wire and subsequent drilling with a cannulated drill. The targeting guide also comprises a keyed telescoping coupling mechanism for connecting the base arm and the attachment fastener arm, which coupling mechanism enables extension of the attachment fastener arm for accommodating varying amounts of soft tissue, while maintaining proper alignment.

In still another aspect, the invention relates to a method for a total reverse hip replacement comprising:
a) implanting an acetabular base having an acetabular bridge by
  i) reaming the human acetabulum using a series of reamers of increasing size, each having a surface comprising a partial spherical shell and an open apex, the open apex preserving the full thickness of the medial acetabular wall, the reaming continuing until a bed of bleeding cancellous bone is reached;
  ii) orienting the acetabular base such that the acetabular bridge is in a substantially anterior to posterior orientation enabling optimal trajectory of acetabular fasteners for attaching the acetabular base to the acetabulum;
  iii) press-fitting the acetabular base into the acetabulum;
  iv) attaching to the acetabular base a target arm for guiding the drilling and placement of fasteners to fasten the acetabular component to the acetabulum, the target arm having guide sleeves concentric and angularly aligned to fastener tunnels within the acetabular bridge;
  v) fastening the acetabular base to the acetabulum;
b) removing the target arm and fixing an acetabular ball into the acetabular base; and
c) implanting a femoral component having a femoral stem portion and a femoral cup portion into a transected femur.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION

The present description is directed in particular to elements forming part of, or cooperating more directly with, apparatus in accordance with the invention. It is to be understood that elements not specifically shown or described may take various forms well known to those skilled in the art.

Figure 1:
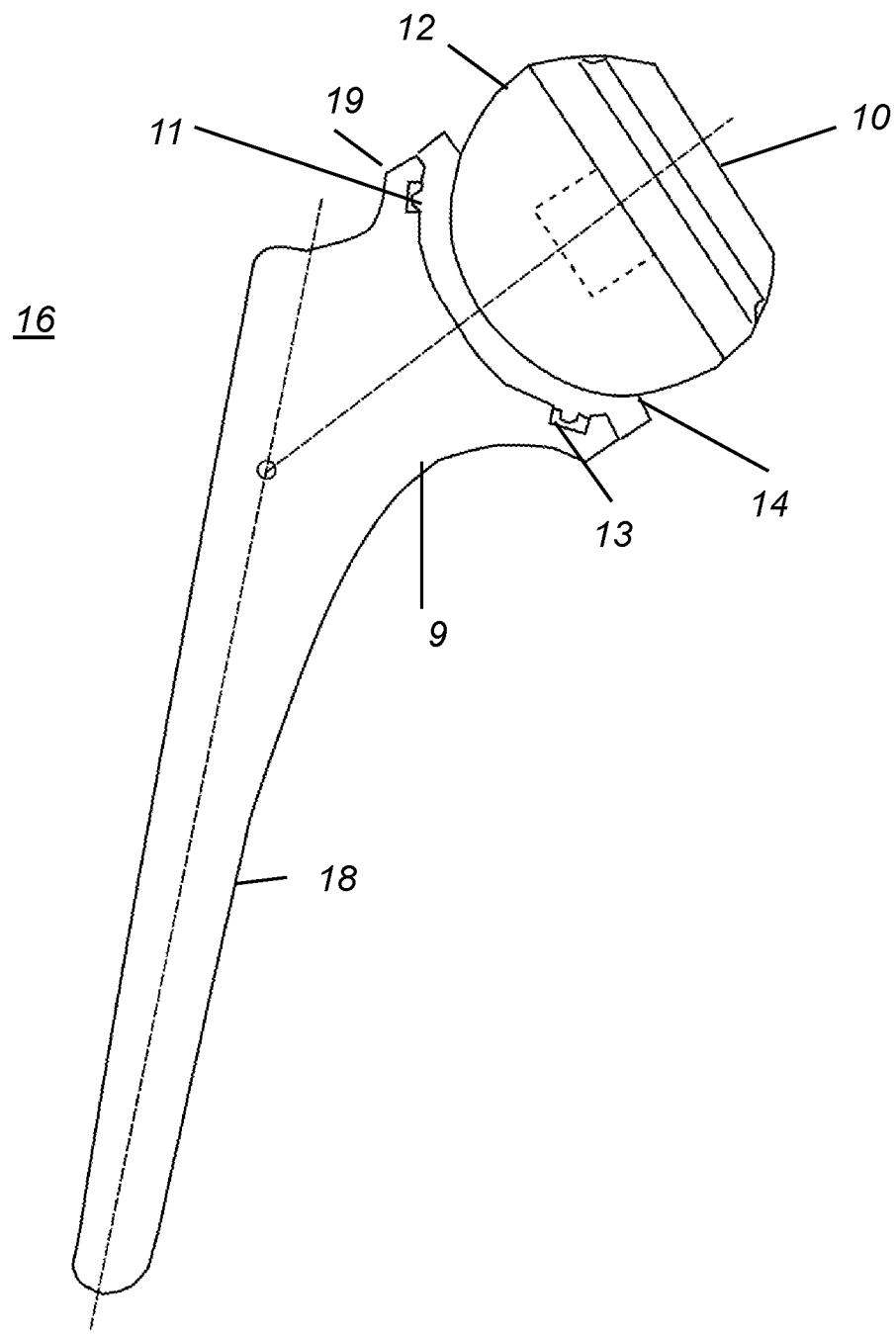
FIG. 1 is a fragmentary perspective view of all of the components in articulation with each as they are in the human body once implanted.

Referring to the Figures, wherein like numerals indicate like parts throughout the several views, attention is first directed to FIG. 1 in which is shown the inventive hip replacement implants as they would articulate in the human hip joint. The femoral component 16 comprises a femoral stem 18, shown in FIG. 1, which would be placed into the human femoral canal and the cup portion 19, shown on FIG. 1, which accepts a saucer shaped spacer 14. The femoral component 16 and spacer 14 replaces the femoral neck and head of a human hip. FIG. 1 shows the femoral component 16 with a shaft 18 to neck 9 angle of 140 degrees. This femoral component shaft to neck angle may vary from 120 to 140 degrees. This range allows for the optimum weight bearing surface contact of the acetabular ball component 12. The femoral component spacer 14 attaches to the mating femoral component cup portion 19, seen in FIG. 1, through a ring 11 and groove 13 fashion. An acetabular ball 12 and a base 10 replaces the articular surface of the acetabulum. The acetabular ball 12 articulates with the spacer 14 of the femoral component 16.

The acetabular component base 10, femoral component stem 18, and alternative femoral component 34 are comprised of suitable bio-compatible materials. The preferred bio-compatible materials include but are not limited to cobalt-chromium alloys, ceramic, titanium and their combinations. Useful ceramic materials include alumina, transformation toughened zirconia, and the like. It is important to achieve a strong bond at the prosthesis-bone interface. The surface character of the prostheses in contact with bone can be exhibit a rough texture to encourage bony in-growth. A hydroxyapatite coating may be applied to the rough prosthesis surfaces to further improve the bone-prosthesis bond via bony on-growth. A cement, for example polymethylmethacrylate (PMMA) cement, may also be employed between the rough prosthesis surface and the bone surface with which it interfaces. Combinations of these approaches for improving the strength of the prosthesis bone interface may also be employed.

Figure 2:
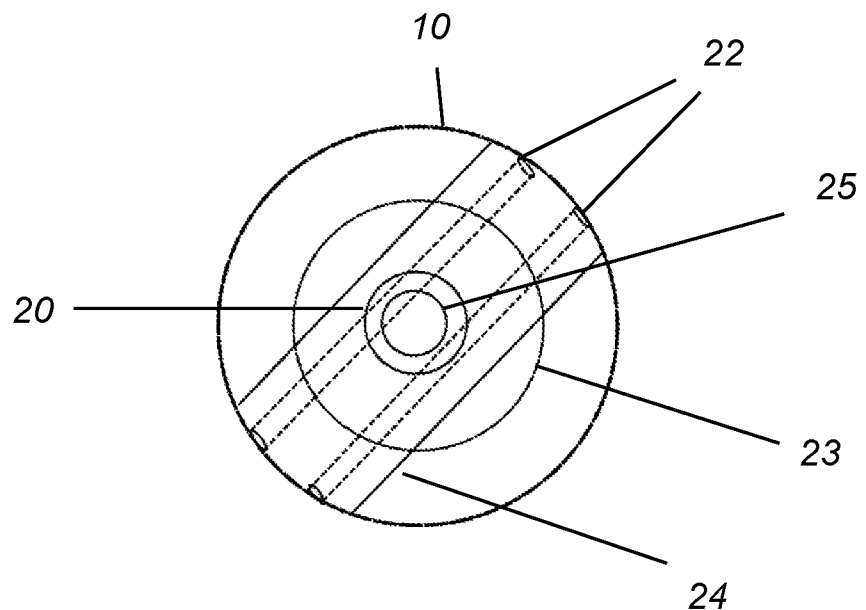
FIG. 2 is a simplified view showing the acetabular base component with an opening at the apex of the cup and a female assembly with keyed depression for targeting guide attachment to central stem.
Figure 7:
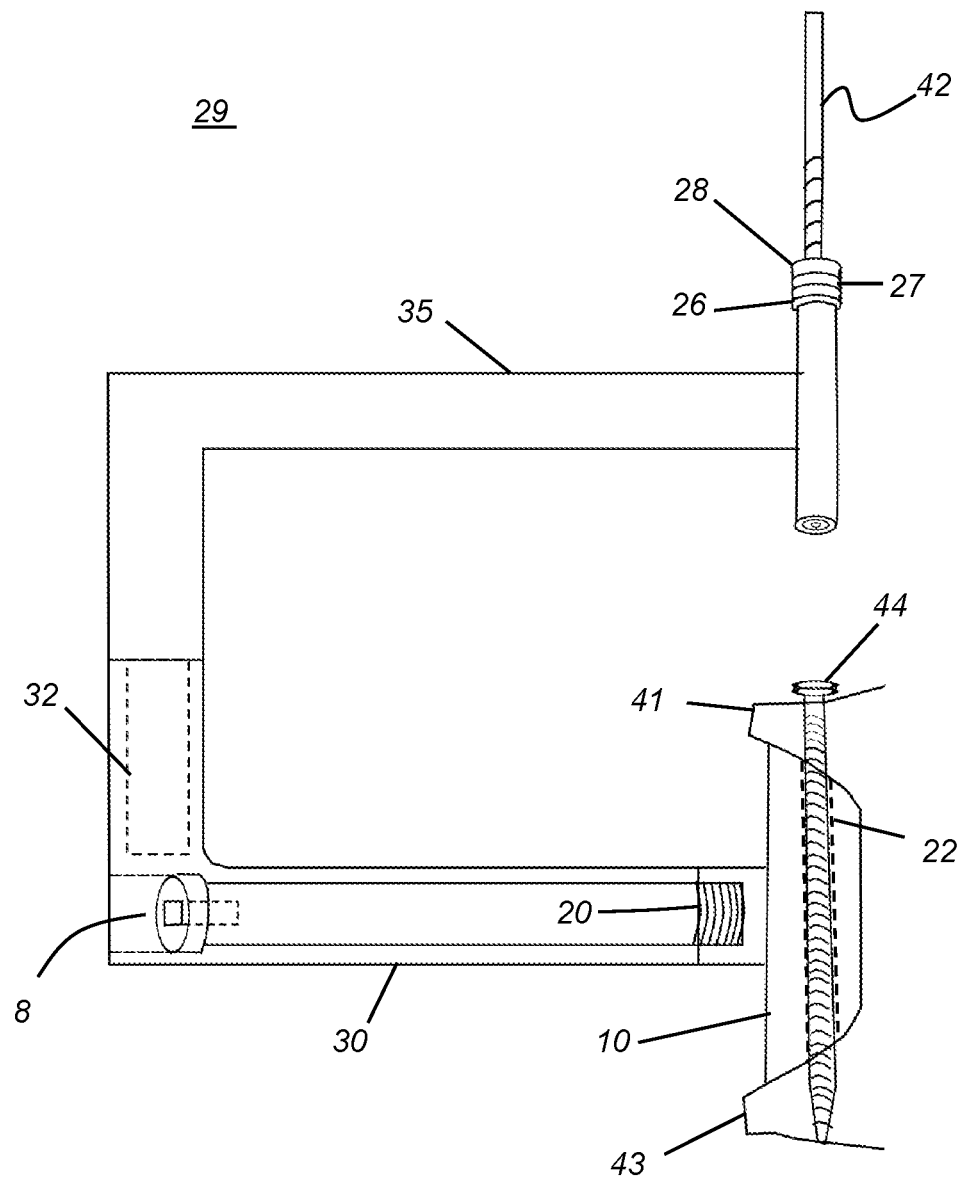
FIG. 7 shows the targeting guide used for accurate placement of the 2 fasteners into the acetabular component.

FIG. 2 shows the acetabular base component from top view. A central barrel 20 having a keyed depression 25, accepts the acetabular ball 12 (not shown in FIG. 2) and an acetabular base arm 30 of targeting guide 29 as shown in FIG. 7. The acetabular base 10 is substantially shaped as a spherical segment, having an opening 23, shown in FIG. 2, at its apex. An acetabular bridge 24 enables structural connection of the acetabular base 10 to the human acetabulum. The acetabular bridge 24 has two tunnels 22 in which two acetabular fasteners 44, for example acetabular screws as shown in FIG. 7, pass through from the targeting arm. Although in FIG. 7, the central barrel 20 having a keyed depression 25 as shown in FIG. 2 is shown to have a screw threading to enable targeting arm attachment, it is understood that other approaches can be employed for the purposes of the invention.

Figure 3:
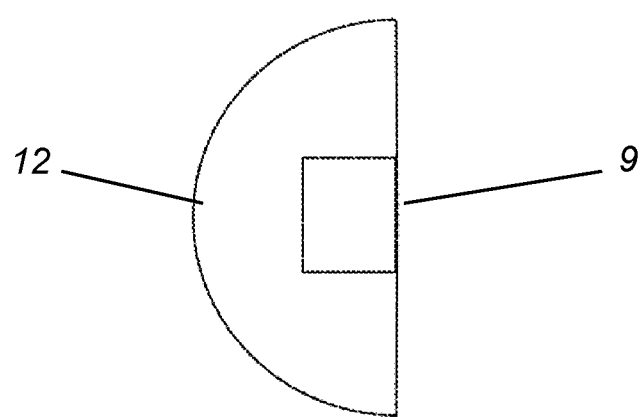
FIG. 3 shows a simplified view of the substantially hemispherical acetabular ball component which articulates with the femoral component cup.

FIG. 3 is a side view of the hemisphere acetabular ball 12 which articulates with the femoral component 16 and spacer 14. The acetabular ball 12 has a cylindrical cavity 9 that engages the central barrel 20. A Morse taper enables these two components to be hammered into place together forming a single engaged unit. Other means of connection of the acetabular base to the acetabular ball include a central screw or press fit with ring and groove, and the like. The engaged component 10 and 12 rest in the human acetabulum.

Figure 4:
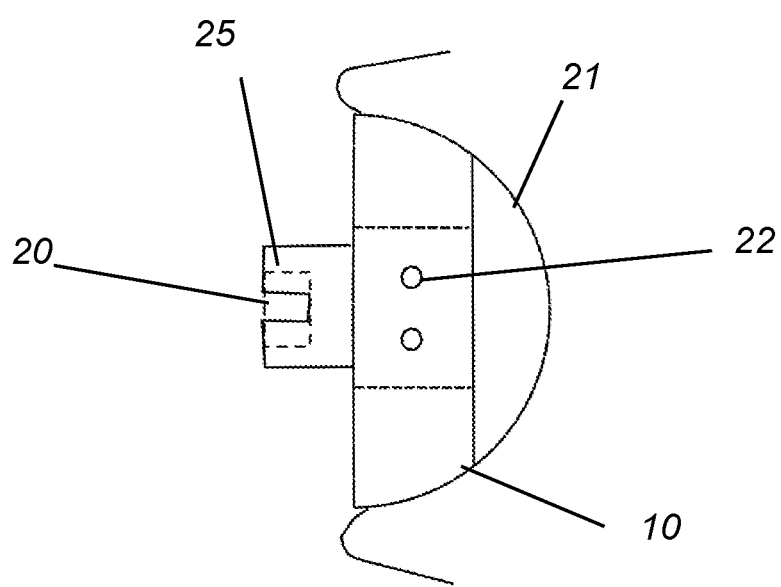
FIG. 4, as in FIG. 2, shows a lateral view of the acetabular base component with and without fastener holes and central stem to mate with the FIG. 3 acetabular ball component.

As shown in FIG. 4, the acetabular base shape at its portion which interfaces to the acetabulum 21 has substantially the shape of a spherical segment. FIG. 4 also shows the entrance points of the two tunnels 22 in which each acetabular fastener 44 (see FIG. 7) passes through the acetabular bridge 24, shown in FIG. 2, thereby enabling fixation of the acetabular base 10 to the human acetabulum. The central barrel 20 is shown as comprising a screw threading and keyed depression 25 which accepts the male attachment of the acetabular base arm 30, shown in FIG. 7. Other means of fixing the acetabular base to the human acetabulum include press fit with oversizing the acetabular base 1-2 mm in diameter when compared to the human acetabulum or screwing lag screws directly into the pelvis through a hole in the spherical portion of the acetabular base.

Figure 5:
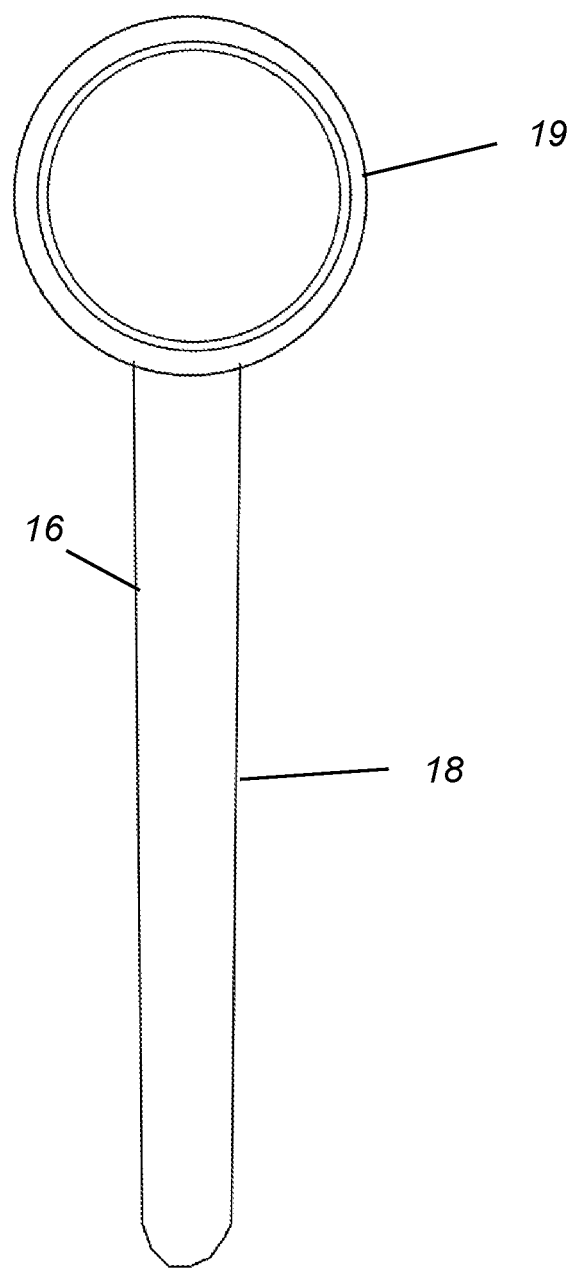
FIG. 5 shows a frontal view of the femoral component with plastic insert liner.

FIG. 5 is a front view of the femoral component 16. This view shows the cup portion 19 that accepts the femoral component spacer 14. The long stem shaped portion 18, of the femoral component 16 is passed into the intramedullary canal of the proximal femur.

Figure 6:
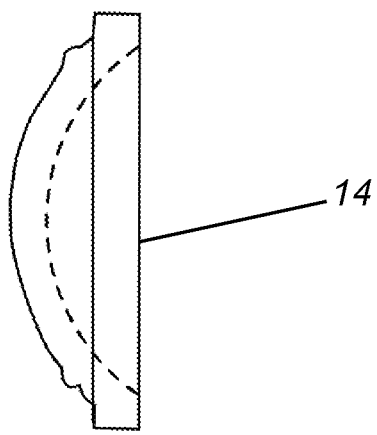
FIG. 6 shows the plastic cup liner detached from the femoral component base.

FIG. 6 is side view of the femoral component spacer 14, which is preferably constructed from a biocompatible polymer material that is resistant to wear as it articulates with the acetabular ball 12 which is generally comprised of metal alloy. Exemplary spacer materials include polyethylene, ultra-high molecular weight polyethylene (UHMWPE), cross linked UHMWPE, and also ceramic, or metal alloy including but not limited to Titanium alloy, Cobalt-Chromium alloy, Alumina-Alumina alloy, Zirconium alloy, and Oxinium alloy. Preferred acetabular ball materials include metal alloy or ceramic. Useful ceramic materials include alumina, transformation toughened zirconia, zirconia toughened alumina, and silicon nitride. In the case where the femoral stem and the femoral cup are both of a metal alloy, they can be formed as a unitary integral element. Similarly, in the case where the femoral stem and the femoral cup are both of a ceramic material they can be formed as a unitary integral element. Further, in the integral ceramic element, the spacer 14 which articulates with the acetabular ball 12, may also be formed integrally.

FIG. 7 shows a side view of a targeting guide 29 that enables the proper alignment for the two acetabular fasteners 44, to be passed through the near wall of the human acetabulum then through the acetabular bridge tunnels 22, and finally into the far human acetabular wall. This effectively seats the acetabular base into the human acetabulum. The targeting guide 29 comprises acetabular base arm 30 that connects to the central barrel 20 of the acetabular base 10 as shown in FIG. 4. An attachment fastener arm 35 removably connects to the acetabular base arm 30 and a keyed telescoping coupling mechanism 32 accommodates the varying amounts of soft tissue in the gluteal region while maintaining proper alignment. In a particular embodiment, the attachment fastener arm 35 includes cannulated fastener guide sleeves 26, 27, 28. The inner most sleeve 28 accommodates a guide wire, not shown. Once guide wire is placed sleeve 28 is removed and sleeve 27 is used to enable a drill 42 for drilling a pilot hole, to pass through it in alignment with the desired trajectory through the acetabulum and through tunnels 22 in the acetabular base shown in FIG. 2. Once the pilot hole is made, sleeve 27 is removed and each of the two acetabular fasteners 44 are passed through the fastener guide sleeve 26 and into the acetabular base 10. The acetabular fasteners 44 gain bony purchase to the human acetabulum in the near wall 41 and the far wall 43 of the human acetabulum. Lastly, the targeting guide 29, shown in FIG. 7 is removed. In another embodiment, only two guide sleeves 27 and 26 are used. Sleeve 27 is used to drill the pilot hole directly into the acetabulum without the use of a guide wire and sleeve 26 is used to aid in alignment for the insertion of acetabular fasteners 44.

Figure 8:
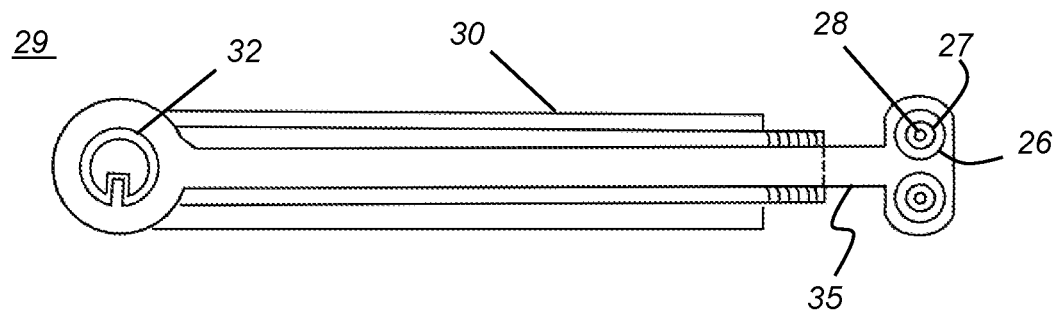
FIG. 8 shows the targeting guide with keyed telescoping arm with dual barrel fastener cannulas.

FIG. 8 is a front view of the targeting arm with a keyed telescoping coupling mechanism 32 that enables extension of the attachment fastener arm. The targeting arm attaches to the acetabular base and the fastener arm 35 holds the sleeves 26, 27, 28. The outer most sleeve, fastener guide 26 is not removable and is adjoined to the attachment fastener arm 35.

Figure 9A:
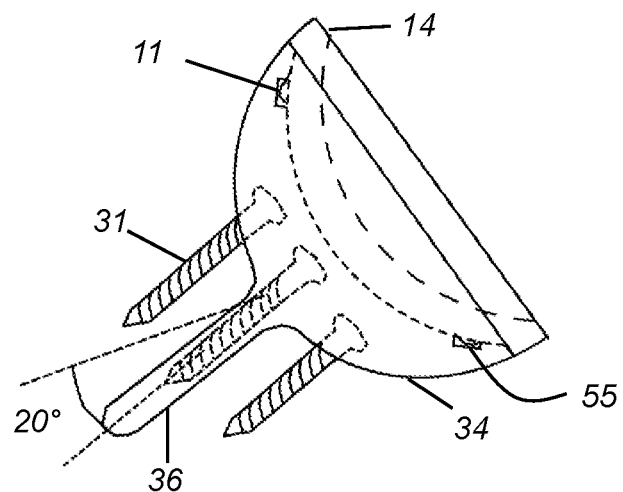
FIG. 9A shows a side view an alternate version of the femoral cup component with 4 locking fasteners and a central post that is housed in the femoral neck.

FIG. 9A is an alternative femoral component 34 that replaces the human femoral head. This femoral component 34 has an advantage in that less bony resection is necessary for its implementation. The alternative femoral component 34 requires a cut through the base of the femoral head, instead of a cut at the base of the femoral neck.

Therefore, the alternative femoral component 34 allows for more bone stock preservation. The alternative femoral component stem 36 may have a variable angle of projection in a 20 degree arc to enable optimum weight bearing contact with the acetabular component 12. The femoral component spacer 14 can be of identical or similar design for the alternative femoral component 34. The alternative femoral component 34 has through holes 40, seen in FIG. 9B, near the apex of the cup to enable fasteners 31, to be placed into the femoral neck thereby gaining bony purchase. The fasteners 31 may be screws, for example locking screws, or compression screws or other suitable fasteners. A preferred number of fasteners 31 and matching holes 40 is 3-4. Preferably, a combination of two locking and two compression screws is used. A femoral neck stem 36 can be press fit into the center of the human femoral neck. The femoral neck stem can be in the range of 0.3-3 cm in diameter and 3-10 cm long. The neck stem 36 is implanted into the femoral neck, and the joint geometry dictates that axis of the neck stem is at an angle with respect to the axis of symmetry of the alternative femoral component 34. The range of useful angles is from about 120 to about 140 degrees. A neck reamer corresponding to the size of the femoral neck stem 36 is used to prepare the human femoral neck to accept neck stem 36.

Figure 9B:
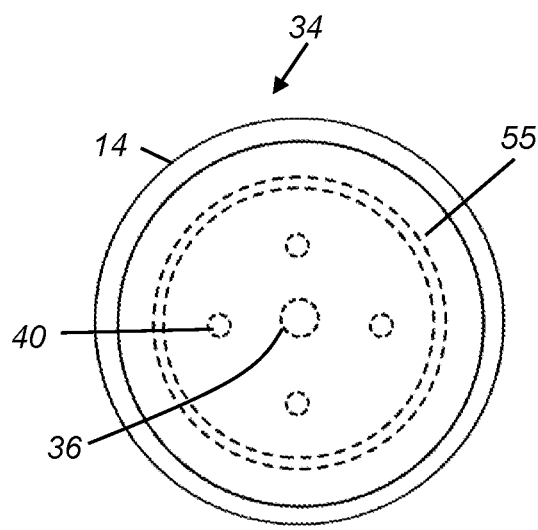
FIG. 9B shows a frontal view of an alternative version of the femoral cup with the central post and 4 locking screw holes for the alternative femoral component cup.

FIG. 9B is a top view of the alternative femoral component which accepts a femoral component spacer 14 and enables the fasteners 31 shown in FIG. 9A to be placed through the cup. Four through holes 40 for fasteners 31 are shown in the embodiment depicted in FIG. 9B. The femoral component spacer 14 attaches to the mating femoral component cup portion 19 (see FIG. 1) through a snap ring 11 and groove 13 fashion. The femoral component spacer 14 attaches to the mating alternative femoral component 34 through a snap ring 11 and groove 55 fashion. The alternative femoral component 34 is preferably made of a metal alloy.

Figure 10A:
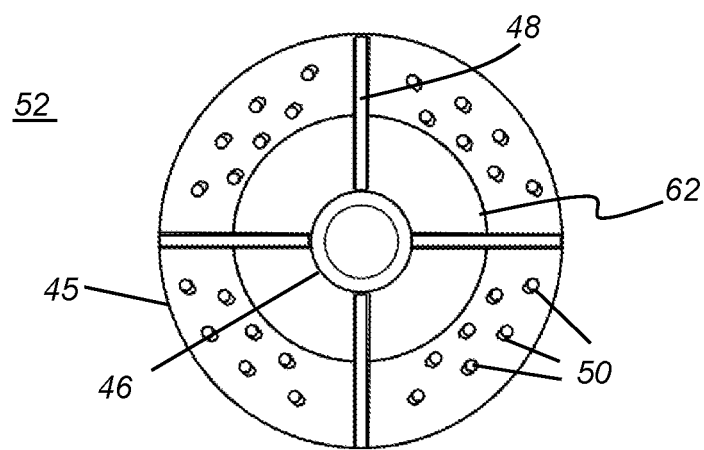
FIG. 10A shows a top view of the open faced acetabular reamer.

FIG. 10A is a top view of the open faced acetabular reamer used to place the acetabular base 10. The reamer having the shape of a spherical segment has an open face 62 at the apex. The surface of the reamer 45, seen on FIG. 10B, has semicircular cutting protrusions 50 that reams the bone of the acetabulum away. In a preferred embodiment, there are 4 radial supports 48 that adjoin to the cylindrical attachment site 46. The attachment site 46 attaches to a stem extension that attaches to a power drill.

Figure 10B:
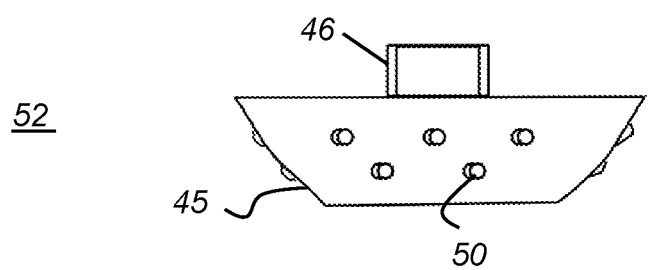
FIG. 10B shows a side view of the open faced acetabular reamer with central attachment.

FIG. 10B is a side view of the open faced acetabular reamer to illustrate the semicircular cutting protrusions 50 of the reamer.

Figure 11:
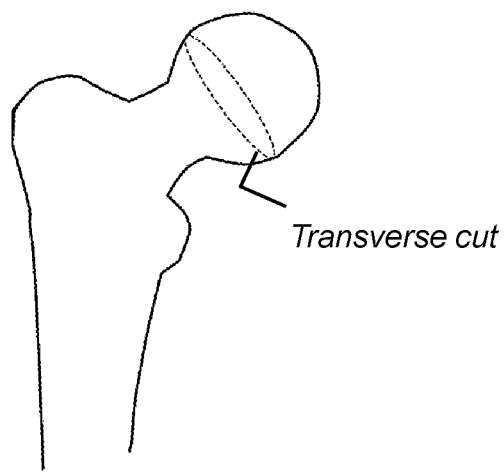
FIG. 11 shows a side view of a proximal femur with the zone of transverse resection of the femoral head marked with dotted lines.
Figure 12:
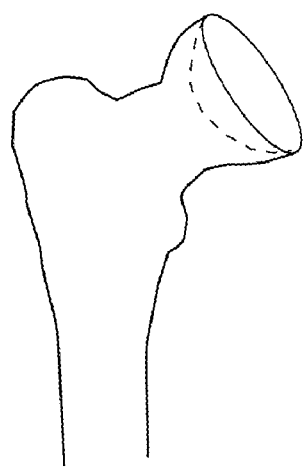
FIG. 12 shows a side view of a proximal femur after the zone of transverse resection has been completed and the reamer has been used to saucerize the femoral head.
Figure 13:
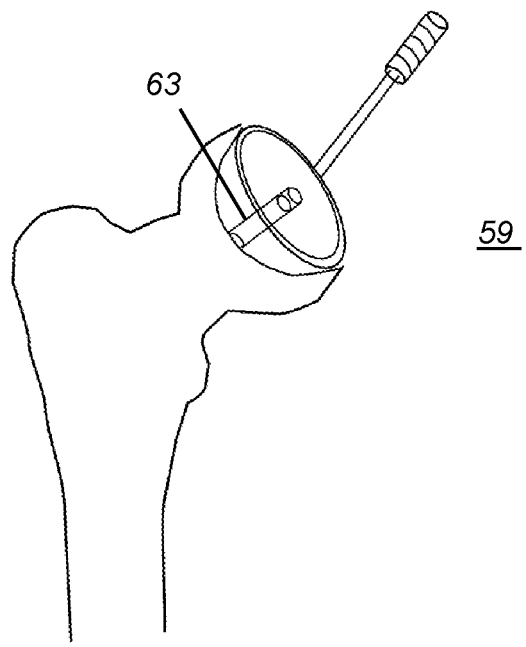
FIG. 13 shows a side view of the post guide used for making the post hole of the central post of the alternative femoral component.
Figure 14:
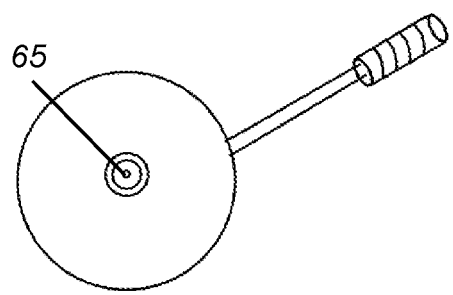
FIG. 14 shows a top view of the post guide with central guide that contains an inner and outer sleeve for application of guide wire and cannulated drill.

A particular method of placing the alternative femoral component begins by making a transverse cut across the approximately central to the approximately proximal third of the femoral head, as shown in FIG. 11. This cut may be made with an oscillating saw. Next the remaining proximal third of the femoral head is saucerized as shown in FIG. 12, using a hemi-spherical reamer that attaches to a stem and power drill. The beginning reamer size matches the smallest component sized diameter. Each reamer is used sequentially in increased diameter until a match is achieved with the desired variably sized component. Next, the post guide 59, shown in FIG. 13, is placed into the saucerized femoral head and a guide wire (not shown) is placed through central guide 63, shown in FIG. 13. Once the guide wire is placed, central sleeve 65, shown in FIG. 14 is removed and a cannulated drill is used whereby drilling is guided by the guide wire and the central guide 63. An alternative method exists to drill through the post guide 59 without previous placement of a guide wire. Next, post guide 59 is removed. Then the alternative femoral component 34 shown in FIG. 9A is hammered into place forming a press fit using an impactor and mallet. Once the alternative femoral component 34 is seated a drill is used to make pilot holes (not shown) in the femoral bone for the four fasteners 31, as shown in FIG. 9B. A cannulated drill guide sleeve similar to that discussed above can be used in through-holes 40 to facilitate the accurate drilling of the pilot holes. Once the fasteners 31 are tightened into place the femoral component spacer 14 is snapped into place using a snap ring and groove design, as shown in FIG. 9A. Similarly, a ceramic spacer would be inserted through a snap ring and groove design.

The method of placement for the acetabular base component begins by using the open faced acetabular reamer 52, shown in FIG. 10B. Starting with the smallest size and sequentially reaming with increasing sized diameter reamers, proceed until a bed of bleeding cancellous bone is reached. The bleeding bed of cancellous is optimal to facilitate bony ingrowth into the porous coated acetabular base component surface that contacts the human acetabular wall. The inventive acetabular reamer 52, having a surface generally comprising a partial spherical shell and an open face 62 as shown in FIG. 10A. Thus reamer 52 does not ream away the thin medial wall of the acetabulum. Once a proper size is reached through reaming, the acetabular base component 10, as shown in FIG. 4, is press fit into position using an impactor that connects to the central barrel 20 and mallet. The acetabular bridge 24 should be oriented in an anterior to posterior or near transverse orientation when impacted, as shown in FIG. 2. This enables proper trajectory of the acetabular fasteners 44. Once the acetabular base component 10 is well-seated, an option exists for extra fixation with fastener/s placed through the acetabular bridge tunnels 22, as shown in FIG. 2.

Once the acetabular base component 10 is well-seated, the targeting arm can be attached to the central barrel 20, as shown in FIG. 7. Once the targeting arm is fastened into place using targeting arm screw 8, attention is taken to the cannulated screw guide sleeves 26, 27, 28, shown in FIG. 7. Optionally, placement of a guide wire, not shown, through the inner most sleeve 28, can be used in the case that acetabular fasteners 44 comprise cannulated screws, not shown, as is known in the art. A retractor is placed posteriorly to protect the sciatic nerve. Once the guide wire is placed through the posterior 41 and anterior 43 walls of the human acetabulum, a pilot hole is drilled, as shown in FIG. 7. The inner most sleeve 28 is removed and a cannulated drill 42 is used to drill the pilot hole along the path of the guide wire. The guide wire passes through the lumen of the cannulated drill and drilling stops once the anterior acetabular wall is breeched. The drill hole is slightly smaller than the diameter of the screw. Next the drill cannula sleeve 27 is removed leaving only the outer screw guide sleeve 26, as shown in FIG. 7. The cannulated acetabular screw 44 passes over the guide wire until the distal tip as shown in FIG. 7 has gained bony purchase in the anterior cortical bone 43 of the human acetabulum. Once the screw/s 44 are placed the targeting arm is removed and the acetabular ball 12 is press fit along the Morris taper of the central barrel 20 with impactor and mallet, as shown in FIG. 1.

The invention has been described in detail, with particular reference to certain embodiments thereof, but it will be understood that variations and modifications can be effected within the spirit and scope of the invention as described above.

What is claimed is:

1. A method for a total reverse hip replacement comprising:
    a) implanting an acetabular base that is formed as a spherical segment having a spherical interface surface that extends between a first flat surface and a second flat surface parallel to the first flat surface and having fastener tunnels that extend in parallel to the first and second flat surfaces and through a bridge portion of the acetabular base, by:
        i) reaming a human acetabulum to reach cancellous bone using a series of reamers of increasing diameter, each reamer having a surface comprising a partial spherical shell and an open apex formed to preserve thickness of a medial acetabular wall;
        ii) orienting the fastener tunnels of the acetabular base to define an anterior-to-posterior fastener trajectory within the acetabulum;
        iii) press-fitting the acetabular base into the acetabulum, according to the defined anterior-to-posterior fastener trajectory;
        iv) fastening the acetabular base to the acetabulum;
    b) fixing a substantially hemispheric acetabular ball into the acetabular base;
    c) implanting, into a transected femur, a femoral stem portion of a femoral component, wherein the femoral component further comprises a cup-shaped portion; and
    d) fitting the cup-shaped portion of the femoral component against the surface of the acetabular ball.

2. The method of claim 1 wherein fixing the acetabular ball into the acetabular base comprises using a tapered fitting.

3. The method of claim 1 wherein fixing the acetabular ball into the acetabular base comprises using a keyed fitting.

4. The method of claim 1 wherein fixing the acetabular ball into the acetabular base comprises using a fastener.

5. The method of claim 1 further comprising attaching a saucer-shaped spacer to the cup-shaped portion of the femoral component.

6. The method of claim 5 wherein attaching the spacer comprises using a snap ring and groove fastening.

7. The method of claim 1 wherein fastening the acetabular base to the acetabulum further comprises:
    attaching a targeting guide to the acetabular base, wherein the targeting guide aligns one or more cannulated guide sleeves to the fastener tunnels of the acetabular base according to the defined fastener trajectory;
    drilling a hole into the acetabulum for each of one or more fasteners, guided by the one or more guide sleeves of the targeting guide, and removing one or more of the guide sleeves;
    attaching a fastener through the drilled hole, guided by one or more remaining guide sleeves.

8. The method of claim 7 wherein attaching the targeting guide comprises using a threaded fitting.

9. The method of claim 7 wherein attaching the targeting guide comprises connecting an arm of the targeting guide to a central barrel that extends outward from the acetabular base.

10. A method for a total reverse hip replacement comprising:
   a) implanting an acetabular base that is formed as a spherical segment having a spherical interface surface that extends between a first flat surface and a second flat surface parallel to the first flat surface and having fastener tunnels through a bridge portion, the tunnels extending in parallel to the first and second flat surfaces by:
      i) reaming a human acetabulum to reach cancellous bone using a series of reamers of increasing diameter, each reamer having a surface comprising a partial spherical shell and an open apex formed to preserve thickness of a medial acetabular wall;
      ii) orienting the tunnels of the acetabular base to define an anterior-to-posterior fastener trajectory within the acetabulum;
      iii) press-fitting the acetabular base into the acetabulum, according to the defined fastener trajectory;
      iv) attaching a targeting guide to the acetabular base, wherein the targeting guide aligns one or more cannulated guide sleeves to the fastener tunnels of the acetabular base according to the defined fastener trajectory;
      v) drilling into the acetabulum for each of one or more fasteners, guided by the one or more guide sleeves of the targeting guide;
      vi) removing one or more of the guide sleeves;
      vii) attaching the one or more fasteners, guided by one or more remaining guide sleeves, to fasten the acetabular base to the acetabulum;
      viii) removing the targeting guide from the acetabular base;
   b) fixing a substantially hemispheric acetabular ball into the acetabular base;
   c) implanting, into a transected femur, a femoral stem portion of a femoral component, wherein the femoral component further comprises a cup-shaped portion; and
   d) fitting the cup-shaped portion of the femoral component against the surface of the acetabular ball.

* * * * *